United States Patent [19]

Tsuda

[11] Patent Number: 4,552,846
[45] Date of Patent: Nov. 12, 1985

[54] ASPARTASE FROM A *BACILLUS SUBTILIS*
[75] Inventor: Yoshihisa Tsuda, Wilmette, Ill.
[73] Assignee: UOP Inc., Des Plaines, Ill.
[21] Appl. No.: 572,108
[22] Filed: Jan. 19, 1984
[51] Int. Cl.$^4$ .......................... C12N 9/88; C12N 1/20; C12R 1/125
[52] U.S. Cl. .................................... 435/232; 435/253; 435/839
[58] Field of Search ................................ 435/232, 253

[56] References Cited

U.S. PATENT DOCUMENTS 3,214,345 10/1965 Chibata et al. .......................... 195/30
3,791,926 2/1974 Chibata et al. .......................... 195/30
4,391,910 7/1983 Kimura et al. ....................... 435/232

*Primary Examiner*—Lionel M. Shapiro
*Attorney, Agent, or Firm*—Thomas K. McBride; William H. Page, II; Eugene I. Snyder

[57] ABSTRACT

A mutant *Bacillus subtilis*, arising from spontaneous adaptation from a parent without detectable aspartase activity, produces recoverable amounts of aspartase. The micro-organism attains maximum growth and enzyme production within about 8 hours and shows excellent glucose tolerance. Aspartase is at least in part produced constitutively, but L-aspartic acid stimulates further aspartase production. The aspartase so produced is readily released from the cell upon cell wall rupture and shows adequate extra-cellular stability for further concentration and purification.

6 Claims, 1 Drawing Figure

ASPARTASE FROM A BACILLUS SUBTILIS

BACKGROUND OF THE INVENTION

Aspartic acid is one of the amino acids used by animals in the synthesis of proteins, and as such only L-aspartic acid is utilized. Although it is not an essential amino acid, which is to say that animals can synthesize this amino acid, it is nonetheless used as a feed additive, especially in Japan where production of synthetic L-aspartic acid in 1978 was 500–1,000 tons. Impacts of Applied Genetics: Micro-Organisms, Plants and Animals, Office of Technology Assessment. Aspartic acid also is used in seasoning industries. But whatever growth in L-aspartic acid production could be expected to result from the aforementioned uses is dwarfed by its anticipated growth as a component in the dipeptide sweetener, L-aspartyl-L-phenylalanine methyl ester. The demand of L-aspartic acid for this use alone is estimated at 1,000 metric tons per year by 1985 and double that by 1990.

A traditional chemical synthesis of L-aspartic acid has been frustrated by the necessity of resolving a racemic mixture, which is too costly to permit a commercially feasible process. Alternately, the obstacle to a total chemical synthesis of L-aspartic acid may be viewed as arising from the absence of a chiral catalyst which selectively synthesizes the L-enantiomer, or which would selectively destroy the D-enantiomer in a racemic mixture. However, nature has provided chiral catalysts in the form of enzymes, and enzymatic methods are the bases of L-aspartic acid production.

Aspartase is an enzyme which catalyzes the conversion of fumaric acid and ammonia to L-aspartic acid, as well as the reverse reaction of deamination of L-aspartic acid, that is,

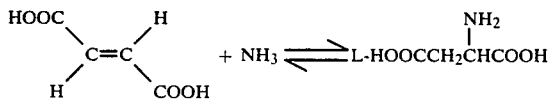

Aspartase itself can be produced by many micro-organisms, although not necessarily in quantities usable for a commercial process. Thus, U.S. Pat. No. 3,214,345 describes a method of producing L-aspartic acid by fermentation in a medium containing fumaric acid and anmonia using micro-organisms including *Pseudomonas fluorescens, Pseudomonas aeroginosa, Bacillus subtilis, Bacillus megatherium, Proteus vulgaris, Escherichia coli* and *Aerobacter aerogenes.* The patentees state that an important and critical feature of their invention is that the fermentation medium be sugar-free. The reason for this limitation is that whereas sugars promote the growth of the micro-organisms they concurrently repress aspartase production. A non-fermentative process for aspartic acid synthesis is decribed in U.S. Pat. No. 3,791,926 where the patentee immobilized an aspartase-producing micro-organism in a matrix formed by polymerizing a water-soluble monomer in an aqueous suspension of microbial cells. In comparing the synthetic methods based on immobilized cells with those based on immobilized aspartase the patentees found that substantial loss of enzyme activity occurred in extraction of aspartase from cells and subsequent concentration of the enzyme from the crude extract. The patentees thus developed and preferred a method of synthesis based on immobilized whole cells to obviate serious disadvantages encountered using immobilized aspartase itself.

In conceptualizing a method for producing L-aspartic acid several criteria can be elaborated. One is that the enzyme should be produced in high yield by a micro-organism which grows quickly using inexpensive growth media under non-stringent biological conditions. Another criterion is that the process should be heterogeneous so as to maximize utilization of aspartase. Because immobilized whole cells impose transport limitations arising both from the matrix itself and from the transport of substrate and product across the cell membrane, a method based on an immobilized enzyme is preferable. However, the latter method has additional requirements including the facile rupture of cell walls to release aspartase, stability of aspartase outside of the cell, and relative ease of purification, or at least concentration, of aspartase without catastrophic loss of enzyme or enzyme activity.

As is discussed more fully herein, I have succeeded in obtaining a micro-organism which grows rapidly under ordinary biological conditions using relatively inexpensive nutrients and which expresses aspartase, in part constitutively, in relatively high yields. The aspartase thus produced can be readily isolated and purified with good recovery, and is immobilized with relatively high efficiency. The resulting immobilized aspartase gives excellent production of L-aspartic acid from fumaric acid and ammonia over its usable lifetime.

An important advantage of the enzyme-producing microorganism of this invention is that maximum enzyme production and microbial growth can be obtained within about 7–8 hours, compared to a period of about 3 days when using a suitable Escherichia coli. Another important advantage, both unexpected and surprising, is that the micro-organism of this invention is quite sugar tolerant, which is to say that aspartase formation is not repressed by sugars even at levels of about 1.0 percent, and in fact aspartase production is increased by sugars such as glucose at levels up to about 1.0 percent. The advantage which accrues from such sugar tolerance is that aspartase can be formed via microbial growth using a relatively cheap and widely available energy source, namely, sugars. Still another advantage is the aspartase produced by the micro-organism of this invention is at least partly constitutive. Thus, although it is desirable to grow the micro-organism in the presence of, for example, L-aspartic acid to maximize enzyme production, L-aspartic acid is not an indispensable requirement for cellular aspartase production.

SUMMARY OF THE INVENTION

The object of this invention is to provide a micro-organism which is a suitable source of aspartase. An embodiment is a micro-organism identified as *Bacillus subtilis*, strain ASP-4, NRRL B-15536. Another embodiment comprises growing the micro-organism identified as the ASP-4 strain of *Bacillus subtilis* NRRL B-15536, especially in the presence of a sugar, so as to produce recoverable amounts of aspartase. Still another embodiment is the aspartase produced by *Bacillus subtilis*, strain ASP-4, NRRL B-15536, when grown arobically in a medium containing an assimilable source of carbon, nitrogen and mineral nutrients at a temperature from about 20° C. to about 45° C. Other embodiments will be apparent from the description herein.

DESCRIPTION OF THE FIGURE

The FIGURE shows several aspects of the fermentation of *Bacillus subtilis*, strain ASP-4, NRRL B-15536, as a function of time. In particular, it shows the depletion of glucose and total nitrogen from the fermentation medium, the cell growth, the production of aspartase, and the fluctuation of pH during the course of fermentation.

DESCRIPTION OF THE INVENTION

In one aspect the invention herein is a biologically pure culture of a strain of *Bacillus subtilis* having the characteristics identifiable with those of NRRL B-15536, said culture being capable of producing in a nutrient culture medium containing a sugar a recoverable amount of an aspartase. In another aspect, the invention is the aspartase produced by the aforementioned micro-organism. Still another aspect of the invention is a method of producing aspartase which comprises growing *Bacillus subtilis*, NRRL B-15536, in a nutrient medium at a temperature from about 20 to about 45° C. and recovering the aspartase produced thereby.

The micro-organism of this invention, *Bacillus subtilis*, strain ASP-4, NRRL B-15536, arose from spontaneous adaptation of a parent strain which manifested no detectable aspartase production. That is to say, several generations of micro-organisms derived from the parent were grown in a medium containing L-aspartic acid and colonies showing good growth were screened for aspartase production. The best producer was given the designation ASP-4 and deposited in the Northern Regional Research Laboratory as NRRL B-15536.

One feature of the mutant of my invention is its rapid cell growth. Thus, for example, in a medium of 2% yeast extract and 1% glucose containing 10 mM each of ammonium sulfate and aspartic acid and 8.3 mM magnesium sulfate at pH 7.2, the micro-organism of this invention showed maximum growth within about 7-8 hours. Since enzyme production coincides with cell growth, which is not the case for all enzyme production, maximum enzyme production also is attained within about 7-8 hours. This compares with *E. coli* where maximum growth and enzyme production is attained only after a period from about 16 hours up to about 3 days.

Cell growth and aspartase production occurs in a nutrient medium containing an assimilable source of carbon, nitrogen and mineral nutrients under aerobic conditions. The nitrogen source is not critical and includes materials such as yeast extract, tryptone, soytone and peptone. Yeast extract appears to optimize aspartase production.

An outstanding feature of the micro-organism of this invention is its tolerance to sugars. Whereas other aspartase-producing micro-organisms have enzyme production strongly repressed by sugars, the micro-organism of this invention not only shows a high tolerance to sugars, but also shows maximum enzyme production in a medium containing about 1.0 percent of a sugar. Among the monosaccharides which can be utilized, cited solely for illustrative purposes, are included glucose, mannose, arabinose, fructose, galactose, and sorbose. Using glucose as an example, the sugar may repress aspartase formation in *E. coli* at levels as low as about 0.1%. In contrast, glucose stimulates formation of aspartase from the micro-organism herein and is preferably present in the medium at a level from about 0.3 to about 1.5 wt. %, especially from about 0.5 to about 1.3 wt. %.

It also has been found that ammonium ion stimulates the production of enzyme. Such stimulation is found in either the presence or absence of aspartic acid, and levels of ammonium ion between about 5 and about 20 mM are advantageously practiced in this invention.

Although the aspartase is at least partly constitutive, that is, the micro-organism produces aspartase even in the absence of an inducer, aspartase production is effectively maximized with small levels of aspartic acid. The presence of from about 5 to about 50 mmoles of aspartic acid per liter of fermentation broth is advantageously used, with a range between about 5 and about 15 being preferred. The optimum amount of aspartic acid depends on other nutrients, for example, the presence of ammonium ion and its concentration, the concentration of sugar, and so forth.

The aspartase produced by ASP-4 can be readily freed by breaking the cell walls and releasing the enzyme into solution. For example, after fermentation is complete cells may be collected, as for example by centrifugation, and washed to remove most of the growth medium. The cells can be resuspended in an aqueous medium and the cell walls ruptured by suitable means. Such methods include sonication, enzyme digestion of the cell wall, and grinding, including homogenization. Cell debris may then be removed, as for example by centrifugation, to give a crude extract containing the aspartase. Aspartase so produced shows a maximum enzyme activity at about 40° C. and at a pH of about 8.5.

The examples which follow illustrate this invention and do not limit it in any way.

EXAMPLE 1

The parent micro-organism, *Bacillus subtilis* 1A1, was obtained from the *Bacillus subtilis* collection center at Ohio State University. This strain showed no detectable aspartase activity. All strains were stored on trypticase agar slants. For selection, the bacteria were grown on a medium containing ammonium sulfate (10 millimolar), magnesium sulfate (2 millimolar), aspartic acid (0.5%), potassium phosphate buffer (10 millimolar) at pH 7.0, and trace amounts of calcium chloride, manganese sulfate, and ferrous sulfate. The micro-organisms were transferred from agar slants to 50 ml. of medium and incubated for a time between about 20 and 24 hours at 32° C. with shaking. After several transfers in the same medium, the organisms were plated onto this medium containing 2% agar, and screening plates were incubated at 30-32° C. for 2 days. Shake cultivations for testing aspartase activity were carried out in 250 ml. conical flasks containing 50 ml. of the above medium supplemented with 1% yeast extract. After cultivation for 16 hours, the bateria were removed by centrifugation at 12,000 rpm for 10 minutes. The cell mixture was resuspended, sonicated to rupture the cell walls, cell debris was removed by centrifugation and the supernatant was analyzed for aspartase activity.

Aspartase activity was assayed using aspartic acid as the substrate. The reaction mixture contained $5 \times 10^{-3}$ molar aspartic acid, $1 \times 10^{-2}$ molar tricine buffer, $2 \times 10^{-4}$ molar magnesium sulfate, and $1 \times 10^{-3}$ molar mercaptoethanol at pH 8.5. 1 ml. of the reaction mixture was placed in the spectrophotometric cell and preincubated in the spectrophotometer for at least 5 minutes at 40° C. A measured amount of supernatant, being the crude enzyme extract, was added to the reaction mixture and the reaction was allowed to proceed for 3 minutes at 40° C. Optical adsorption was measured every 60 seconds at 240 nm. One unit of aspartase activity is defined as 1 micromole of fumaric acid formed per minute. Protein was estimated by the biuret reaction with bovine serum albumin as the standard. The strain ASP-4 was selected for its high aspartase activity by this method.

ASP-4 was grown on a medium containing 2% yeast extract, 1% glucose, 10 mM ammonium sulfate, 10 mM aspartic acid, and 8.3 mM magnesium sulfate (1 g/L) at a pH of 7.0 at 37° C. Some growth characteristics in a 10 liter fermenter are reproduced in the FIGURE. Growth rates were determined by measuring the dry weight of bacteria using an analytical microwave oven after washing the cells twice with water. Glucose in the medium was determined using a Beckmann glucose analyzer. Among the features demonstrated by the FIGURE are maximum growth within about 8 hours, enzyme production which coincides with cell growth, and utilization of glucose without repression of aspartase formation. Whereas maximum growth rate is exhibited at 37° C., one-half the maximum occurs at 25° C.

EXAMPLE 2

Effect of Glucose Concentration

The effect of sugar concentration, as exemplified by glucose, on aspartase production is summarized below in Table 1. Two organic nitrogen sources were used to show that such an effect was general.

TABLE 1

Effect of Glucose on Aspartase Production

| Glucose (%) | Organic Nitrogen (%) | Activity (Units/ml) | Total Act. (Units) | Specific Act. (Units/mg protein) |
|---|---|---|---|---|
| Yeast Extract | | | | |
| 0 | 0.5 | 3.0 | 36.4 | 5.5 |
| 0.5 | 0.5 | 8.1 | 97.3 | 8.4 |
| 1.0 | 0.5 | 10.9 | 130.8 | 10.3 |
| 2.0 | 0.5 | 3.0 | 36.0 | 2.8 |
| Tryptone | | | | |
| 0 | 0.5 | 1.5 | 18.0 | 2.2 |
| 0.5 | 0.5 | — | — | — |
| 1.0 | 0.5 | 16.4 | 196.8 | 16.2 |
| 2.0 | 0.5 | 5.7 | 68.4 | 6.6 |

In *E. coli* aspartase synthesis, the presence of glucose in amounts as little as 0.1% strongly suppresses the production of the enzyme. This clearly shows that aspartase production by ASP-4 has the important advantage over that by *E. coli* being capable of using a cheap and readily available carbon source.

EXAMPLE 3

Effect of Nitrogen Sources and Aspartic Acid

A significant amount of aspartase was synthesized when the ASP-4 strain was grown in the medium which contained only 0.5% yeast extract as a nitrogen source. However, aspartase production increased proportional to the concentration of aspartic acid in the culture medium. The increase in specific activity of the enzyme was more drastic, with an improvement of seven-fold in the production of aspartase.

In the absence of aspartic acid in the medium, ammonium sulfate was utilized well at a concentration of 5 mM for the production of aspartic acid. An increase in ammonium sulfate concentration up to 20 mM diminished aspartase production. When both ammonium sulfate and aspartic acid were present in the medium together with 0.5% yeast extract enzyme production was maximized at 10 mM of each of ammonium sulfate and aspartic acid. An increase in either of them inhibited aspartase production. Tables 2–show the effect of various nitrogen sources and of aspartic acid on the production of aspartase by ASP-4.

TABLE 2

Effect of Organic Nitrogen Source on Aspartase Production

| Organic Nitrogen Source (0.5%) | Aspartate (mM) | Glucose (%) | Activity (Units/mL) | Specific Activity (Units/mg) | Total Activity (Units) |
|---|---|---|---|---|---|
| Yeast Extract (Sigma) | 0 | 1.0 | 7.7 | 9.6 | 92.4 |
| Yeast Extract | 10 | 1.0 | 17.5 | 17.2 | 210.0 |
| Soytone (Difco) | 0 | 1.0 | 7.8 | 9.4 | 93.6 |
| Soytone | 10 | 1.0 | 21.0 | 18.3 | 252.0 |
| Tryptone (Difco) | 0 | 1.0 | 1.6 | 2.2 | 19.2 |
| Tryptone | 10 | 1.0 | 26.1 | 22.5 | 313.2 |
| Peptone (Difco) | 0 | 1.0 | 7.7 | 11.7 | 92.4 |
| Peptone | 10 | 1.0 | 15.5 | 17.2 | 186.0 |

TABLE 3

Effect on $(NH_4)_2SO_4$ and Aspartic Acid on Aspartase Production

| $(NH_4)_2SO_4$ (mM) | Aspartic Acid (mM) | Yeast Extract (%) | Activity (Units/mL) | Specific Activity (Units/mg) | Total Activity (Units) |
|---|---|---|---|---|---|
| 0 | 0 | 0.5 | 2.1 | 1.6 | 25.2 |
| 0 | 5.0 | 0.5 | 4.3 | 6.0 | 51.6 |
| 0 | 10.0 | 0.5 | 6.7 | 9.5 | 80.4 |
| 0 | 20.0 | 0.5 | 7.6 | 11.4 | 91.2 |
| 5.0 | 0 | 0.5 | 7.4 | 9.2 | 88.8 |
| 10.0 | 0 | 0.5 | 5.1 | 6.4 | 61.2 |
| 20.0 | 0 | 0.5 | 3.2 | 5.1 | 38.4 |
| 5 | 10 | 0.5 | 19.0 | 15.9 | 228 |
| 5 | 20 | 0.5 | 15.0 | 12.6 | 180 |
| 10 | 10 | 0.5 | 20.0 | 16.9 | 240 |
| 10 | 20 | 0.5 | 14.2 | 11.9 | 170 |
| 20 | 10 | 0.5 | 18.4 | 15.1 | 221 |
| 20 | 20 | 0.5 | 13.5 | 11.3 | 162 |

TABLE 4

Effect of Yeast Extract and Tryptone on Aspartase Production[a]

| Yeast Extract (%) | Tryptone (%) | Activity Units/ml | Total Activity (Units) | Specific Activity Units/mg |
|---|---|---|---|---|
| 0.5 | 0 | 6.3 | 76 | 7.6 |
| 1.0 | 0 | 9.1 | 110 | 8.3 |
| 1.5 | 0 | 24.9 | 291 | 19.8 |
| 2.0 | 0 | 27.0 | 324 | 18.6 |
| 0 | 0.5 | 7.5 | 90 | 9.1 |
| 0 | 1.0 | 9.1 | 109 | 10.1 |
| 0 | 1.5 | 11.7 | 140 | 12.1 |
| 0 | 2.0 | 9.0 | 108 | 9.3 |

[a]All media contained 1% glucose, 10 mM $(NH_4)_2SO_4$, and 10 mM aspartic acid.

EXAMPLE 4

The activity of the free aspartase was measured as a function of temperature and pH. These results are summarized in Table 5. In both tests a crude enzyme preparation was obtained as follows. Cells were suspended in a 0.05 M phosphate buffer, pH 7.0, containing $1 \times 10^{-3}$ M MgSO$_4$ and $1 \times 10^{-3}$ M mercaptoethanol and ruptured by sonication. Debris was removed by centrifugation at 13,000 rpm for 30 minutes, and the clear liquid used directly as the crude extract.

TABLE 5

| Effect of Temperature (°C.) and pH on Aspartase Activity | | | | | | | |
|---|---|---|---|---|---|---|---|
| Activity (units/mL at 40° C.) | 0.65 | 1.90 | 2.55 | 2.85 | 3.35 | 1.60 | 1.30 |
| pH | 7.0 | 7.75 | 8.0 | 8.25 | 8.5 | 8.75 | 9.0 |
| Activity (units/mL, pH 8.5) | 1.70 | 3.60 | 3.90 | 4.20 | 4.50 | 4.20 | 3.60 | 2.60 |
| T, °C. | 23 | 31 | 35 | 38 | 41 | 44 | 48 | 51 |

These data show that aspartase activity is maximized at about 41° C., with denaturation occurring rapidly at temperatures in excess thereof, and at a pH of 8.5.

What is claimed is:

1. A biologically pure culture of a strain of *Bacillus subtilis* NRRL B-15536, said culture being capable of producing in a nutrient medium containing a sugar a recoverable amount of an aspartase.

2. A method of producing aspartase comprising growing aerobically *Bacillus subtilis* NRRL B-15536 in a medium containing an assimilable source of carbon, nitrogen and mineral nutrients at a temperature from about 20 to about 45° C., and recovering the aspartase produced thereby.

3. The method of claim 2 where the medium contains from about 5 to about 50 mmoles per liter of L-aspartic acid.

4. The method of claim 3 where the medium contains from about 5 to about 15 mmoles per liter of L-aspartic acid.

5. The method of claim 2 where the medium contains from about 0.3 to 1.5 wt. % of glucose.

6. The method of claim 5 where the medium contains from about 0.5 to about 1.3% glucose.

* * * * *